US008763611B2

(12) United States Patent
Seitz et al.

(10) Patent No.: US 8,763,611 B2
(45) Date of Patent: Jul. 1, 2014

(54) LOW-PROFILE CPR MASK

(75) Inventors: Nicholas R. Seitz, Dayton, OH (US); Michael B. Laycox, Dayton, OH (US); Trent B. Shroyer, Dayton, OH (US)

(73) Assignee: S&S Medical Products, LLC, Dayton, OH (US)

( * ) Notice: Subject to any disclaimer, the term of this patent is extended or adjusted under 35 U.S.C. 154(b) by 774 days.

(21) Appl. No.: 11/741,140

(22) Filed: Apr. 27, 2007

(65) Prior Publication Data

US 2007/0251528 A1 Nov. 1, 2007

Related U.S. Application Data

(60) Provisional application No. 60/795,438, filed on Apr. 27, 2006.

(51) Int. Cl.
*A61M 16/06* (2006.01)
*A62B 18/02* (2006.01)

(52) U.S. Cl.
CPC ............... *A61M 16/06* (2013.01); *A62B 18/02* (2013.01)
USPC ............ 128/206.28; 128/206.21; 128/205.25; 128/202.28

(58) Field of Classification Search
CPC ...... A61M 16/06; A61M 2016/06–2016/0661; A62B 18/00; A62B 18/02; A62B 18/025; A62B 18/06
USPC ............. 128/206.21–207.13, 205.25, 203.29, 128/201.23–201.25, 202.28–203.11
See application file for complete search history.

(56) References Cited

U.S. PATENT DOCUMENTS

| | | | | |
|---|---|---|---|---|
| 2,995,131 | A * | 8/1961 | Elam et al. | 128/202.28 |
| 4,226,234 | A * | 10/1980 | Gunderson | 128/205.24 |
| 4,354,488 | A * | 10/1982 | Bartos | 128/205.25 |
| 4,655,213 | A * | 4/1987 | Rapoport et al. | 128/205.25 |
| 5,121,745 | A | 6/1992 | Israel | |
| 5,143,061 | A * | 9/1992 | Kaimer | 128/206.24 |
| 5,146,914 | A | 9/1992 | Sturrock | |
| 5,291,880 | A * | 3/1994 | Almovist et al. | 128/201.22 |
| 5,555,569 | A * | 9/1996 | Lane | 2/424 |
| 6,044,844 | A * | 4/2000 | Kwok et al. | 128/207.11 |
| 6,386,198 | B1 * | 5/2002 | Rugless | 128/206.21 |
| 6,691,703 | B2 | 2/2004 | McKinney et al. | |
| 6,968,844 | B2 | 11/2005 | Liland et al. | |
| 2002/0020414 | A1 * | 2/2002 | Fukunaga | 128/205.13 |
| 2003/0000532 | A1 * | 1/2003 | Bowman et al. | 128/206.21 |
| 2003/0024532 | A1 * | 2/2003 | Sniadach | 128/205.13 |
| 2003/0172932 | A1 * | 9/2003 | Matioc | 128/206.24 |
| 2003/0178025 | A1 * | 9/2003 | Holt et al. | 128/205.13 |
| 2003/0217746 | A1 * | 11/2003 | Gradon et al. | 128/201.26 |
| 2006/0060199 | A1 * | 3/2006 | Lampotang et al. | 128/205.13 |

OTHER PUBLICATIONS

Segan, Ross D., et al, "A Discussion of the Issue of Football Helmet Removal in Suspected Cervical Spine Injuries", 1993, Journal of Athletic Training, vol. 28, No. 4, pp. 294-305.*
Photographs and Directions for Use for "Pocket Mask" by Laerdal (1993).

* cited by examiner

*Primary Examiner* — Valerie L Skorupa
(74) *Attorney, Agent, or Firm* — Thompson Hine LLP

(57) ABSTRACT

A low profile CPR mask shaped to fit under the face mask of a victim allows immediate emergency ventilation without requiring the helmet be removed. The mask may be molded to fit ergonomically to a rescuer's palm and be pliable upon the application of moderate force to obtain a tight-fitting mask seal against the victim's face.

18 Claims, 4 Drawing Sheets

LOW-PROFILE CPR MASK

CROSS REFERENCE TO RELATED APPLICATION

This application claims the benefit of U.S. Provisional Application Ser. No. 60/795,438 filed on Apr. 27, 2006.

BACKGROUND

The disclosure is directed to a cardiopulmonary resuscitation (CPR) patient mask, and more particularly, to a low-profile CPR mask.

CPR protocol dictates that where a head, neck or spinal injury is suspected the head and neck of the victim of an injury should not be moved. Furthermore, if the victim is not breathing, immediate initiation of rescue breathing (for example, by mouth-to-mouth resuscitation) by trained personnel is required. For activities such as football, hockey, auto racing, motorcycle racing or the like, participants typically wear a protective helmet that includes face protection (for example, a face mask or a cage). Unfortunately, current resuscitation mask designs are shaped such that a face mask or helmet with face protection worn by a victim must first be removed in order to access the victim's mouth to initiate rescue breathing. Conventional masks are usually retained in their proper position during use by straps that extend behind the head of the victim. In order to provide enhanced head protection, typically a face mask is not removably attached to the helmet. For helmets having a removable face mask, removal often requires special tools that would delay the response by a rescuer to start lifesaving airflow to a victim having a suspected head, neck or spinal injury.

Accordingly, there is a need for a low-profile CPR mask shaped to fit under a face mask worn by a victim and that does not require removal of a victim's headgear for attachment of straps and the like to secure the mask to the victim.

SUMMARY

This disclosure describes a low profile CPR mask shaped to fit under the face mask of a helmet worn by victim. The low profile shape of the mask allows immediate emergency ventilation to begin without requiring the helmet to be removed first from the victim. The mask may be molded to fit ergonomically to a rescuer's palm and may be made of a material that is pliable upon the application of moderate force to obtain a tight-fitting mask seal against the victim's face.

DETAILED DESCRIPTION

Figure 1:
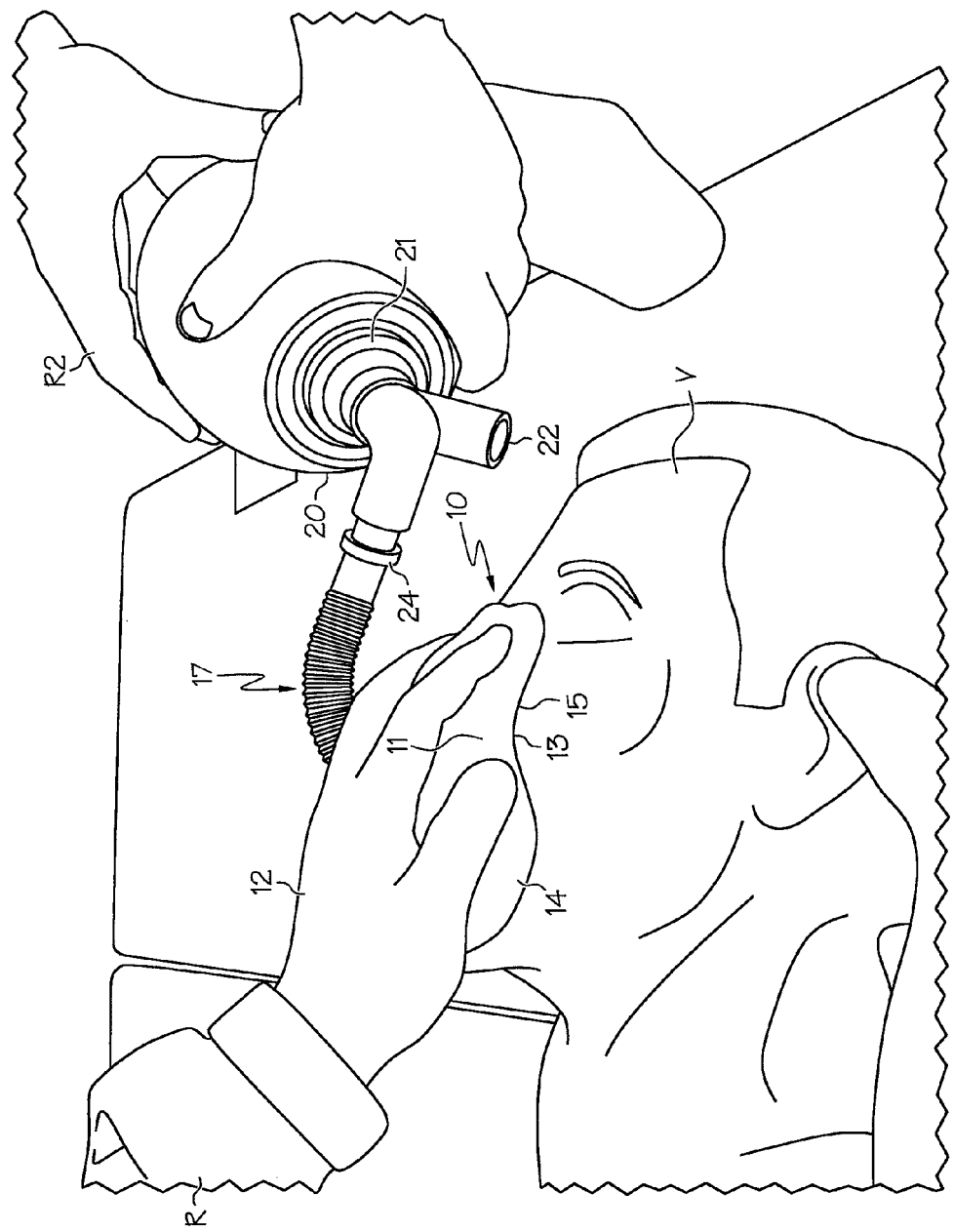
FIG. 1 is a perspective view of an embodiment of the disclosed low-profile CPR mask placed over a victim's face.

As shown in FIG. 1, an embodiment of the disclosed low-profile CPR mask, generally designated 10, may be used to effect rescue breathing, mouth-to-mouth resuscitation or any other CPR procedure requiring emergency breathing assistance. The outer surface 11 of the mask 10 may be shaped to receive the palm and fingers of a rescuer's hand 12 and the inner surface 13 shaped about its periphery 14 to conform to the face 15 of a victim V upon the application of moderate force to obtain a tight-fitting mask seal.

A ventilation tube, generally designated 17, may be attached to an integral exit port 18 (see FIGS. 3 and 4) protruding from the side of the mask 10 and oxygen-rich air may be supplied by manually squeezing resilient air bladder 20 connected to the ventilation tube 17. Bladder 20 includes valve assembly 21 having air inlet 22 that allows fresh air to enter the bladder 20 and an exhaust valve 24, preferably mounted on tubing 17, through which air is forced through the ventilation tubing 17 and into the mask 10 when the bladder 20 is squeezed. Valve assembly 21 may be in the form of a one-way valve, wherein fresh, ambient air to the victim V is drawn into bladder 20 when the bladder 20 inflates and the fresh air in the bladder 20 is forced through exhaust valve 24, through tubing 17 and into the mask 10, and from the mask 10 to the victim V when the bladder 20 is squeezed. Thus, exhaust valve 24 preferably is a one-way valve that prevents exhaled air from victim V from traveling back through the tube 17. Alternatively, the rescuer R, or a second rescuer R2 (see FIG. 1) may blow into a mouthpiece 26 (see FIGS. 3 and 4) formed in the distal end of tubing 17, thereby forcing air through the tube 17, exhaust valve 24 and into the mask 10 to ventilate the victim V.

Figure 2:
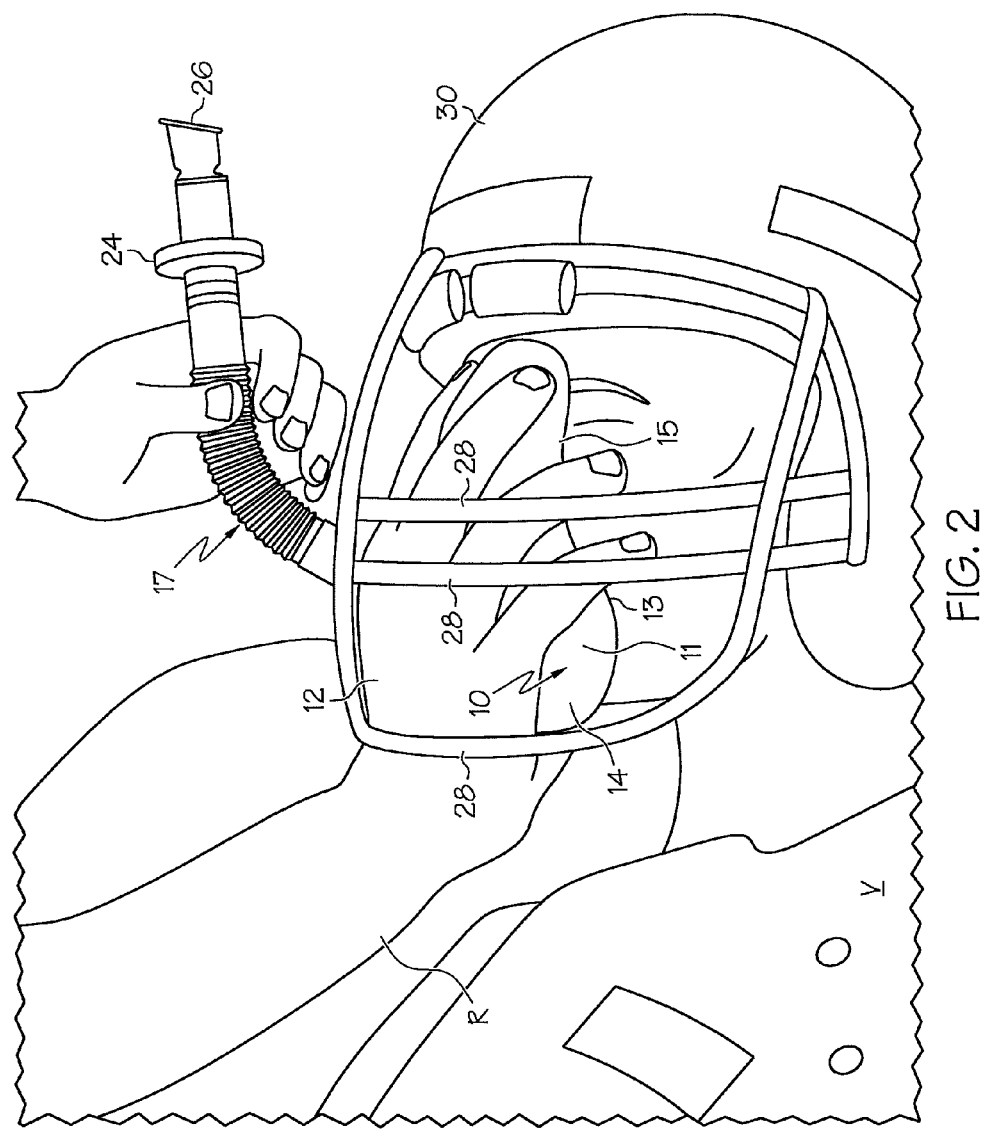
FIG. 2 is a perspective view of the mask of FIG. 1 placed under the face mask of a helmet worn by a victim.

As shown in FIG. 2, rescuer R has placed CPR mask 10 over the nose and mouth of a victim V to initiate immediate emergency ventilation to victim V. The CPR mask 10 may be shaped to slip between the face mask 28 of a helmet 30 (for example, football helmet 30) and the face 15 of the victim V. Furthermore, the mask 10 may be shaped to receive the palm of a rescuer's hand 12 and conform to the victim's face 15 upon application of moderate force to obtain a substantially air-tight seal against the victim's face 15. Ventilation may be supplied by rescuer R by manually blowing into the mouthpiece 26. It should be noted that the mask 10 as disclosed may be used to provide emergency ventilation for victims who have the sustained a head, neck or spinal injury in the course of a wide range of activities (for example, football) where the participants commonly wear a protective helmet that includes face protection. Alternatively, rescuer R may operate bladder 20 (shown in FIG. 1) to ventilate the victim V.

Figure 3:
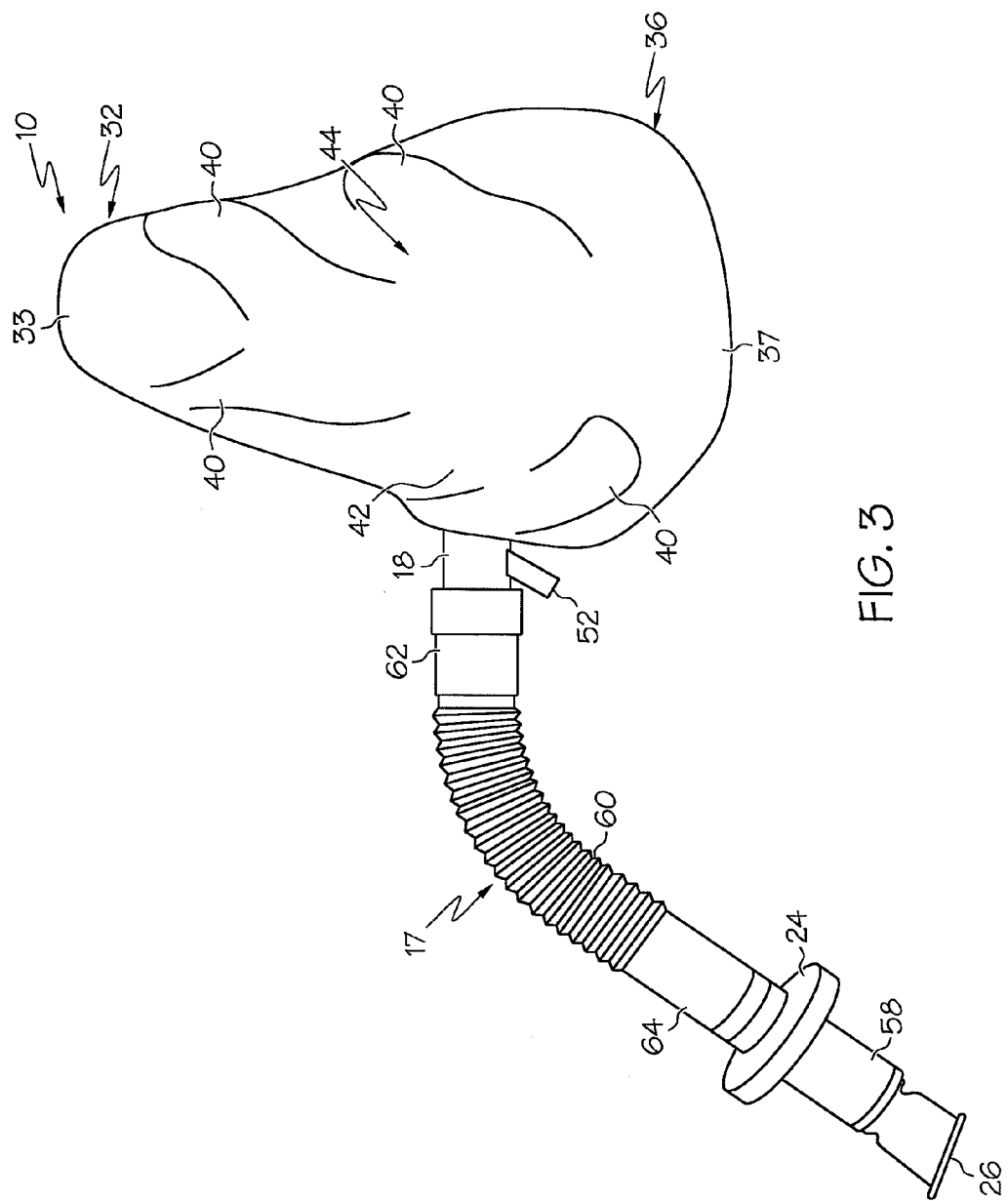
FIG. 3 is a front elevational view of the embodiment of the low-profile CPR mask of FIG. 1.
Figure 4:
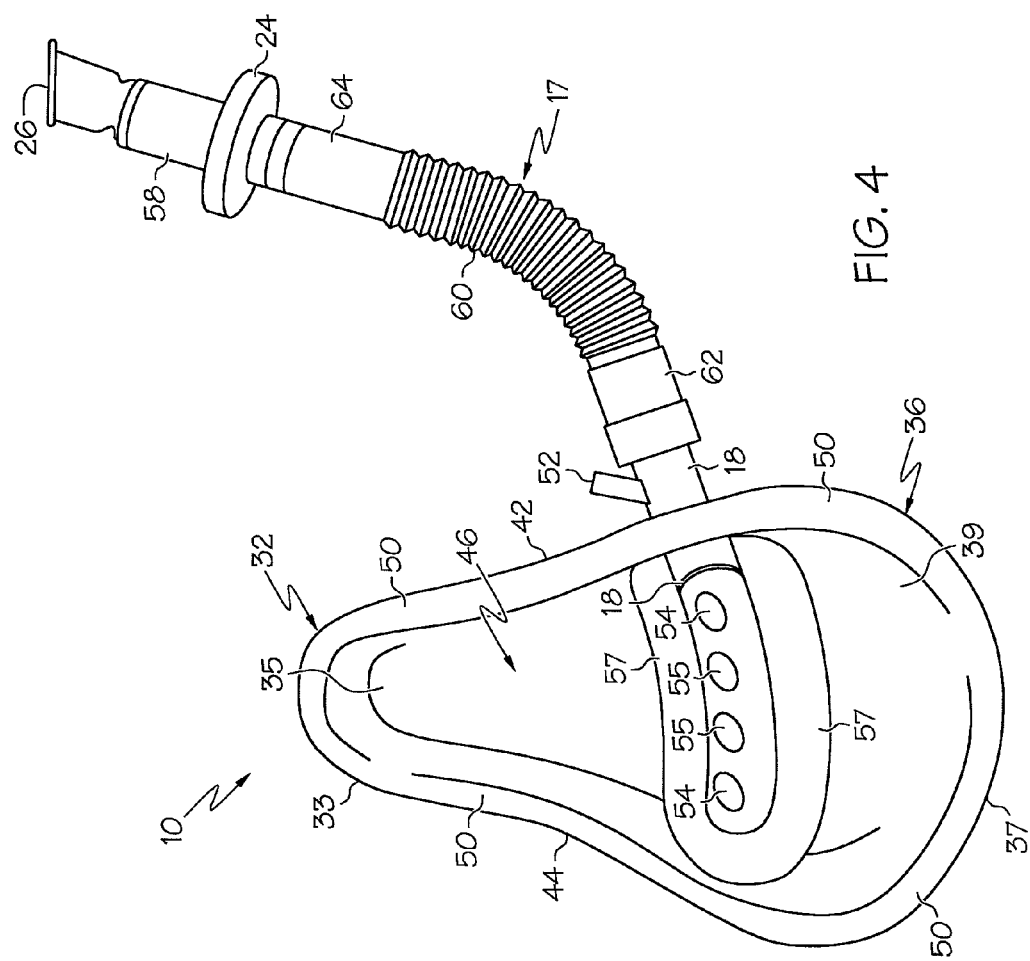
FIG. 4 is a rear elevational view of the embodiment of the low-profile CPR mask of FIG. 3.

As shown in FIGS. 3 and 4, the mask 10 may contain a nose-fitting section, generally designated 32, and a chin-fitting section, generally designated 36. The nose-fitting section 32 may comprise an outer surface 33 facing away from the victim V (see FIGS. 1 and 2) and an inner surface 35 facing the victim V. Likewise, the chin-fitting section 36 may comprise an outer surface 37 facing away from the victim V and an inner surface 39 facing the victim V. The nose-fitting section 32 and chin-fitting section 36 may be constructed from the same material or alternatively from different materials suitable for CPR applications. Likewise, the outer surfaces 33, 37 and inner surfaces 35, 39 may be constructed from the same material or alternatively from different materials suitable for CPR applications.

It should be noted that the mask 10 may be formed in different sizes (for example, adult size, youth size, or child size) to accommodate size of the face of the victim V (see FIGS. 1 and 2). The different sizes may be characterized by the relative longitudinal distances between the nose-fitting section 32 and the chin-fitting section 36 of the mask 10. Alternatively, the different sizes may be characterized by the relative width distances, or a combination of the relative longitudinal and relative width distances. A plurality of masks 10 may be shaped to be nested and thereby occupy a minimal amount of space, for instance, storage space in an ambulance or athletic trainer's bag.

As shown in FIG. 3, mask 10 may include longitudinally extending grooves shaped to form finger ridges 40 that may be integrated into the outer surface 33 to receive a rescuer's palm and fingers, thereby providing the mask 10 with a stable gripping surface to provide the rescuer with complete placement control of the mask 10. The exit port 18 that protrudes from the side 42 of the mask 10 may be adapted to fit any standard CPR ventilation tubing and be constructed of any material suitable for CPR fittings.

As shown in FIGS. 3 and 4, the disclosed low-profile CPR mask 10 comprises relatively rigid plastic body sections 44, 46 and a relatively flexible plastic rim 50 (i.e., typically known as an "aircuff" in the art) extending about the periphery of the mask 10 that conforms to facial contours to make a substantially air-tight seal with the victim's face V. The flexible rim 50 preferably may be disposed to extend outwardly away from the inner surface 35. The flexible rim 50 may be attached to the rigid body 46 by any conventional means, such as, for example, dielectric welding or RF frequency welding. The flexible rim 50 can be made from various suitable materials, for example rubber latex, silicon or polyvinyl chloride (PVC). The material of the flexible rim 50 may be further characterized as being deformable upon the application of a moderate force. The rigid body sections, generally denoted 44, 46 of the mask 10, may be made of various suitable materials, such as but not limited to nylon and rubber latex. It should be noted that the rigid body sections 44, 46 may be constructed from the same material, or alternatively, from different materials attached together by any conventional means and suitable for CPR applications.

When the rescuer R uses the mask 10 on a victim V whose facial anatomy is particularly difficult (e.g., the victim V has a pointed chin) the mask 10 may be flexed to the shape of the chin by pressing the body 44, 46 together using sufficient force applied through the fingers and palm of the rescuer's hand 12. This force distorts the chin section 36 in a manner such that the body 44, 46 adapts to the shape of the chin. Furthermore, the flexible rim 50 material seals to the victim's face 15.

As shown in FIGS. 3 and 4, the ventilation tube, generally denoted 17, comprises a plurality of ventilation tubing sections and ventilation tubing fittings. The ventilation tubing fittings include an exhaust valve 24, a mouthpiece 26, and a sealable exit port 18, wherein the exit port 18 includes an integrally formed oxygen supply port 52 shaped to connect directly to bottled oxygen if desired to treat the victim V. Although alternatively, the ventilation tube 17, exhaust valve 24 and mouthpiece 26 may be a one-piece, rigid construction and may be configured to swivel 180° at the exit port 18 to provide "hands-free" management of the tube 17 to the rescuer R. It should be noted that for normal operation, the oxygen supply port 52 remains in a sealed configuration.

As shown in FIG. 4, the mask 10 includes a relatively rigid perforated section 54 located adjacent the inner surface 35 and connected to exit port 18 that guides air entering the mask 10 to the mouth and nose of the victim V. Perforated section 54 includes a plurality of perforations 55 to direct incoming ventilating air into the victim's nose and mouth. The mask 10 further includes a raised surface gutter 57 disposed approximately adjacent the perforated tubing 54. The surface gutter 57 may be raised approximately ¼ inch in height to securely hold the perforated tubing 54 in place. The tube 17 includes a mouthpiece tube 58, disposed between the exhaust valve 24 and the mouthpiece 26; and a section of ribbed, flexible section 60 disposed between open ends 62, 64, wherein end 62 receives exit port 18, and end 64 receives exhaust valve 24. Ribbed section 60 allows some movement in a longitudinal direction which retards longitudinal movement at the exit port 18 connection and the exhaust valve 24 connection. The ventilation tube 17 may be constructed of any material suitable for CPR tubing.

The ventilation tube 17 may have a typical length dimension of about 5 to 36 inches, more typically about 5 to 24 inches, and even more typically about 5 to 12 inches. Typically, the ventilation tube orifice portions have diameter suitable to slidably receive the plug portions of the ventilation tube valves 18, 24. Typically, the plug portion of the valve may be press fit into the orifice portion of the tubing although any connection means resistive to longitudinal movement may be used.

Having described the invention in detail and by reference to the preferred embodiments, it will be apparent that modifications and variations thereof are possible without departing from the scope of this disclosure.

What is claimed is:

1. A low profile CPR mask comprising:
    a nose-fitting section and a chin-fitting section that together form a generally convex outer surface of a mask that faces away from a wearer and an inner surface that faces the wearer, the chin-fitting section being shaped to conform to a palm of a rescuer's hand;
    a rim extending about the periphery of the mask, the rim being capable of forming a seal with the wearer's face; and
    an opening therein disposed in a side of the mask and configured to receive an exit port such that the exit port does not interfere with the placement of the palm of the rescuer's hand on the chin-fitting section, wherein the opening is disposed nearer to the rim than to an apex of the generally convex outer surface;
    wherein the outer surface of the nose-fitting section includes elongate grooves extending longitudinally from a central portion of the mask to an outer edge of the mask on a left or right side thereof, the elongate grooves positioned and oriented such that when the palm of the rescuer's hand is positioned on the chin-fitting section, an elongate portion of the fingers of the rescuer's hand are received in the elongate grooves.

2. The low profile CPR mask of claim 1 further comprising an exit port received in the opening in the side of the mask, wherein the exit port is shaped to receive a ventilation tube leading away from the outside surface of the mask and receive a tube leading into the inner surface of the mask.

3. The low profile CPR mask of claim 2 further comprising the tube leading to the inner surface of the mask; wherein the tube terminates as a perforated section that includes perforations positioned to direct incoming ventilating air into the victim's nose and mouth.

4. The low profile CPR mask of claim 3 further comprises a raised surface gutter positioned adjacent to the perforated section.

5. The low profile CPR mask of claim 2 wherein the exit port includes an oxygen supply port disposed exterior to the side of the mask.

6. The low profile CPR mask of claim 2 further comprises the ventilating tube connected to the exit port.

7. The low profile CPR mask of claim 6 wherein the ventilating tube includes an exhaust valve near an end of ventilating tube that is distal relative to the mask.

8. The low profile CPR mask of claim 1 wherein the mask, at least from a top view, is generally-pear shaped.

9. The low profile CPR mask of claim 1 wherein the inner surface of the mask includes an aircuff about its outer peripheral edge that contacts the face of the wearer.

10. The low profile CPR mask of claim 1 wherein the outer surface of the nose-fitting section and a portion of the chin-fitting section both include elongate grooves to receive the fingers of a rescuer's hand.

11. The low profile CPR mask of claim 1 further comprising a rigid body section that includes the nose-fitting section and the chin-fitting section.

12. A method of providing emergency ventilation to a victim in need of CPR wearing a helmet having a facemask or faceguard comprising:
   providing a CPR mask comprising:
      a nose-fitting section and a chin-fitting section that together form a generally convex outer surface of a mask that faces away from the victim and an inner surface that faces the victim, the chin-fitting section being shaped to conform to a palm of a rescuer's hand;
      a rim extending about the periphery of the mask, the rim being capable of forming a seal with the victim's face; and
      an opening therein disposed in a side of the mask and configured to receive an exit port such that the exit port does not interfere with the placement of the palm of the rescuer's hand on the chin-fitting section, wherein the opening is disposed nearer to the rim than to an apex of the generally convex outer surface;
      wherein the outer surface of the nose-fitting section includes elongate grooves extending longitudinally from a central portion of the mask to an outer edge of the mask on a left or right side thereof, the elongate grooves positioned and oriented such that when the palm of the rescuer's hand is positioned on the chin-fitting section, an elongate portion of the fingers of the rescuer's hand are received in the elongate grooves;
   placing the CPR mask over the nose and mouth of the face of the victim without displacing the facemask or faceguard;
   attaching a ventilating tube to the mask;
   applying force with the hand of a rescuer to the mask to obtain a substantially air-tight seal against the victim's face; and
   conveying air through the ventilating tube and into the mask to ventilate the victim.

13. The method of claim 12 wherein the CPR mask is placed underneath the facemask and over the nose and mouth of the victim.

14. The method of claim 12 wherein the CPR mask is placed between the faceguard and over the nose and mouth of the victim.

15. The method of claim 12, wherein during the applying force step, the palm of the rescuer's hand is positioned on the chin-fitting section and an elongate portion of the fingers of the rescuer's hand are received in the elongate grooves.

16. A low profile CPR mask comprising:
   a nose-fitting section and a chin-fitting section that together form an outer surface of a mask that faces away from a wearer and an inner surface that faces the wearer, the chin-fitting section being shaped to conform to a palm of a rescuer's hand, and at least the nose-fitting section having ergonomic elongate grooves extending longitudinally from a central portion of the mask to an outer edge of the mask on a left or right side thereof, the elongate grooves positioned and oriented to conform with a longitudinal length of an elongate portion of one or more fingers of the rescuer's hand when the palm of the rescuer's hand is positioned on the chin-fitting section; and
   an opening therein disposed in a side of the mask and configured to receive an exit port such that the exit port does not interfere with the placement of the palm of the rescuer's hand on the chin-fitting section and the one or more fingers of the rescuer's hand in the ergonomic elongate grooves on the nose-fitting section;
   wherein a major portion of the outer surface, which includes an outermost convex portion thereof, is uninterrupted by an opening or a ventilation component and is adapted such that, in use, a central portion of the rescuer's hand cups unobstructedly thereover.

17. The low profile CPR mask of claim 16 wherein the chin-fitting section includes one or more ergonomic elongate grooves shaped to conform to an elongate portion of a finger, a thumb, or both of the rescuer's hand.

18. The low profile CPR mask of claim 16 further comprising a rigid body section that includes the nose-fitting section and the chin-fitting section.

* * * * *